United States Patent [19]

Hasegawa

[11] 4,212,813
[45] Jul. 15, 1980

[54] PROCESS FOR PRODUCING SUBSTITUTED OR UNSUBSTITUTED NAPHTHALIC ACIDS AND ACID ANHYDRIDES THEREOF

[75] Inventor: Ryoichi Hasegawa, Yono, Japan

[73] Assignee: Nippon Kayaku Kabushiki Kaisha, Tokyo, Japan

[21] Appl. No.: 950,407

[22] Filed: Oct. 11, 1978

[51] Int. Cl.$^2$ ............................................... C07B 3/00
[52] U.S. Cl. ............................. 260/346.4; 260/507 R; 260/687 R; 562/408
[58] Field of Search ............ 260/346.4, 507 R, 687 R; 562/408

[56] References Cited

U.S. PATENT DOCUMENTS

| | | | |
|---|---|---|---|
| 2,578,759 | 12/1951 | Straley et al. | 260/345.2 |
| 2,833,816 | 5/1958 | Saffer et al. | 260/345.2 |
| 2,966,513 | 12/1960 | Fields | 562/408 |

FOREIGN PATENT DOCUMENTS 35-12931 9/1960 Japan .
50-142543 11/1975 Japan .
50-142544 11/1975 Japan .

OTHER PUBLICATIONS

Tkacheva et al., Chemical Abstracts, vol. 87 (1977), 134788t.
Digurov et al., Chemical Abstracts, vol. 74 (1971), 124535a.
Hasebe et al., Chemical Abstracts, vol. 77 (1972), 75048v.
Digurov et al., Chemical Abstracts, vol. 76 (1972), 140298x.
Digurov et al., Chemical Abstracts, vol. 75 (1971), 88369j.
Plakidn et al., Chemical Abstracts, vol. 75 (1971), 5568z.
Marx et al., Chemical Abstracts, vol. 69 (1968), 18912h.
Rogovik et al., Chemical Abstracts, vol. 69 (1968), 18911g.

*Primary Examiner*—Richard Raymond
*Attorney, Agent, or Firm*—Stevens, Davis, Miller & Mosher

[57] ABSTRACT

Process for producing substituted or unsubstituted naphthalic acids and acid anhydrides thereof by oxidation of corresponding acenaphthenes whose naphthalene nucleus may have one or two substituents from the group consisting of halogens, sulfonic acid groups, sulfonate groups, and nitro. The oxidation is performed at 30°–150° C. using molecular oxygen in the presence of (1) at least one heavy metal compound, such as cobalt acetate or manganese acetate, in an amount of 0.005–0.3 mole per mole of said acenaphthenes or a mixture of heavy metal compounds in that amount and a bromine compound in the range of $5 \times 10^{-5}$ to $2 \times 10^{-1}$ mole/liter of reaction solution as a catalyst and (2) at least one accelerator selected from the group consisting of lower fatty acid anhydrides, ketones and aldehydes, whereby side reactions such as condensation can be suppressed to a satisfactory extent, thereby leading to an improvement in yield of final product. A subsequent treatment of the oxidation product obtained by this process with peroxides, hypohalogenates, or molecular oxygen results in a higher yield.

12 Claims, No Drawings

PROCESS FOR PRODUCING SUBSTITUTED OR UNSUBSTITUTED NAPHTHALIC ACIDS AND ACID ANHYDRIDES THEREOF

BACKGROUND OF THE INVENTION

1. Field of the Invention

This invention relates to a process for producing substituted or unsubstituted naphthalic acids and acid anhydrides thereof by oxidation of corresponding acenaphthenes whose naphthalene nucleus may have one or two substituents selected from the group consisting of a halogen atom, a sulfonic acid group or sulfonate group, and a nitro group.

2. The Prior Art

In the oxidation of acenaphthenes into corresponding naphthalic acids, it is the common practice to use chromates, bichromates, permanganates or nitric acid as oxidizing agents. However, the use of these oxidizing agents involves several disadvantages in that they are expensive and there is a possibility that environmental pollution may be caused by contamination with the heavy metals or with nitrogen oxides.

Several processes of producing naphthalic acid by oxidation of acenaphthene per se are known including processes as described in U.S. Pat. No. 2,966,513 and Japanese Patent Publication No. 12931/60, in which molecular oxygen is used for the oxidation in the presence of heavy metal compounds and bromide as catalyst. In these processes, however, the oxidation is carried out under extremely high temperature and high pressure and the reaction is continued under the same severe conditions even after the absorption of oxygen has been stopped, requiring very great care to the safety of operation (and, particularly, to the explosion limit of the gas phase). In this sense, the processes using such severe reaction conditions are disadvantageous from an industrial viewpoint.

U.S. Pat. No. 2,578,759 describes another process of oxidizing acenaphthene with molecular oxygen in the presence of a catalyst of a heavy metal compound and an accelerator.

In Example 1 of this Patent specification, there is an example wherein 110 parts of acenaphthene are oxidized in 1500 parts of propionic acid which is mixed with 108 parts of cobalt acetate and 375 parts of butyl aldehyde, thereby giving naphthalic acid. In this process, the cobalt acetate is used in a large amount, i.e. in a quantity equimolar to the acenaphthene, causing problems encountered in recovery and regeneration of the cobalt catalyst.

As will be seen from the above, the prior art techniques of oxidizing acenaphthene have important defects.

On the other hand, there are known several processes of oxidizing substituted acenaphthenes including, aside from the afore-mentioned processes using bichromates, etc., as oxidizing agents, processes such as described in Japanese provisional publications Nos. 142543/75 and 142544/75, in which molecular oxygen is used for oxidation in the presence of heavy metal compounds and bromides. In these processes, however, it is essential to use the starting substituted acenaphthenes in very dilute concentrations (e.g. when 5,6-dichloroacenaphthene is used, its concentration in the reaction solution must be below 0.045 moles/l) so as to attain good yield. In all the Examples concerning the production of 4,5-dichloronaphthalic acid, the yield of 4,5-dichloronaphthalic acid is below 4.36 g per liter of the reaction vessel. Similarly, in all the Examples concerning the production of 4-sulfonaphthalic acid, the yield per liter of the reaction vessel is below 9.66 g. In addition, the yield of naphthlic acid per liter of the vessel is below 10.3 g as clearly described in Examples of Japanese provisional publication No. 142544/75. Thus, it seems very difficult to reduce the processes into practice because of their poor productive capacity.

In the previously mentioned U.S. Pat. No. 2,578,759, there is no description concerning the oxidation of acenaphthenes substituted with a halogen atom, a sulfo group or a nitro group. Presumably, this is because, in the oxidation of acenaphthenes substituted with a halogen atom, a sulfo group or a nitro group, side reactions such as condensation tend to take place and the oxidation reaction is impeded to a considerable extent as compared with that of unsubstituted acenaphthenes partly due to the fact that starting substituted acenaphthenes per se and intermediates thereof produced during the oxidation reaction are generally low in solubility in organic solvents (and particularly, in lower fatty acids).

When we made an experiment in which an acenaphthene derivative, e.g. 5,6-dichloroacenaphthene, was oxidized in accordance with the procedure of Example 1 of U.S. Pat. No. 2,578,759 which procedure was proposed to oxidize unsubstituted acenaphthene, we found that, since the amount of cobalt acetate used as the catalyst was so great, the reaction conditions became severe, a large amount of a condensation product of 5,6-dichloroacenaphthene was secondarily produced and the oxidation reaction stopped on the way, so that satisfactory results could not be obtained with regard to yield and purity.

As will be understood from the foregoing, the prior art processes of oxidizing acenaphthene or substituted acenaphthenes into corresponding naphthalic acids require very severe reaction conditions such as high temperature and high pressure or the use of very large amounts of heavy metal compounds, or result in poor conversion of acenaphthenes.

SUMMARY OF THE INVENTION

It has been now found that the oxidation of acenaphthenes with molecular oxygen in the presence of a catalyst of a heavy metal compound is feasible under mild conditions using an accelerator, whereby side reactions such as condensation can be suppressed to a satisfactory extent, thereby leading to an improvement in yield of final product. It has been also found that a subsequent treatment of the oxidation product obtained by this process with peroxides, hypohalogenates or molecular oxygen results in higher yield.

Thus, according to one aspect of the present invention, there is provided a process for producing naphthalic acids or acid anhydrides thereof, which comprises oxidizing acenaphthenes with or without one or two substituents selected from the group consisting of a halogen atom, a sulfonic acid group or sulfonate, and a nitro group attached to the naphthalene nucleus thereof with molecular oxygen in at least one organic solvent, in the presence of (1) at least one heavy metal compound or a mixture of a heavy metal compound and a bromine compound as a catalyst and (2) at least one compound selected from the group consisting of lower fatty acid anhydrides, ketones, and aldehydes (first stage oxidation).

According to another aspect of the present invention, there is provided a process for producing naphthalic acids or acid anhydrides thereof in higher yield in which the oxidation product obtained in the first stage oxidation is further oxidized with peroxides, hypohalogenates or molecular oxygen in an aqueous alkali solution or a mixture of the alkali solution with an organic solvent (second stage oxidation).

Acenaphthenes suitable as the starting materials for the practice of the invention include, for example, acenaphthene, 4-chloroacenaphthene, 5-chloroacenaphthene, 4,6-dichloroacenaphthene, 5,6-dichloroacenaphthene, 4,7-dichloroacenaphthene, 4-bromoacenaphthene, 5-bromoacenaphthene, 5,6-dibromoacenaphthene, 4-sulfoacenaphthene, 5-sulfoacenaphthene, 4-nitroacenaphthene, 5-nitroacenaphthene, 4,6-dinitroacenaphthene, 5,6-dinitroacenaphthene, 4,7-dinitroacenaphthene, 4-sulfo-5-chloroacenaphthene, 4-chloro-5-sulfoacenaphthene, 5-chloro-6-sulfoacenaphthene, 4-chloro-6-sulfoacenaphthene, 4-sulfo-6-nitroacenaphthene, 4-nitro-6-sulfoacenaphthene, 4-nitro-5-chloroacenaphthene, 4-chloro-5-nitroacenaphthene, 4-chloro-6-nitroacenaphthene, and the like.

In these, a preferable acenaphthene is a member selected from the group consisting of 5,6-dichloroacenaphthene, 5-chloroacenaphthene, 5-bromo-acenaphthene and sodium acenaphthene-5-sulfonate.

The heavy metal compounds used as a catalyst in the first stage oxidation include, for example, salts, oxides or hydroxides of metals such as Co, Mn, Cr, Ce, Ni, Rh, Pd, Pt, Ir and the like. Of these, the metal salts of fatty acids containing 2 to 10 carbon atoms such as acetic acid or propionic acid and naphthenic acid are preferred and the salts such as cobalt acetate and manganese acetate are most preferable. Though these metal compounds may be used in combination, the cobalt compounds may preferably be used as one component to obtain good results. The most preferable heavy metal compound catalyst is a mixture of cobalt and manganese salts. If used in combination, the atomic ratio of cobalt to a metal other than cobalt should preferably be in the range of 1:0.001-2.

The concentration of the heavy metal compound in the reaction solution is generally in the range of 0.003 to 0.1 moles/l and the heavy metal compound is used in an amount of 0.005 to 0.3 moles, preferably 0.02 to 0.04 moles, per mole of the acenaphthenes.

Examples of the bromine compounds are inorganic compounds such as HBr, $Br_2$, LiBr, NaBr, KBr, $CaBr_2$, $BaBr_2$, $CoBr_2$, $NiBr_2$, $MnBr_2$, $NH_4Br$ and the like, and organic compounds such as tetrabromoethane, dibromoacrylic acid, monobromoacetic acid, benzyl bromide and the like. Of these, the alkali metal bromides or alkaline earth metal bromides are preferable. In order to obtain good results, the concentration of the bromine compound in the reaction solution is generally in the range of $5 \times 10^{-5}$ to $2 \times 10^{-1}$ moles/l and the bromine compound is used in an amount of 0.1 to 2.5 moles per mole of heavy metal compounds. A preferable catalytic system according to the present invention is the mixture which comprises, a Co salt and a Mn salt, and an alkali metal bromide or an alkaline earth metal bromide.

The accelerators useful in the present invention are, for example, lower fatty acid anhydrides such as acetic anhydride, propionic anhydride, and maleic anhydride and the like, ketones such as methyl ethyl ketone, methyl isopropyl ketone and the like, and aldehydes such as acetaldehyde, paraformaldehyde and the like. Preferably, the lower fatty acid anhydrides are used and acetic anhydride is most preferable. The accelerator is used in an amount of 0.1 to 10 moles, preferably 0.2 to 2 moles, per mole of acenaphthenes. The accelerator is added to the reaction system either continuously or discontinuously during the reaction.

The organic solvents useful for the reaction include, for example, lower fatty acids such as acetic acid, propionic acid, butyric acid, and the like, aromatic solvents such as benzene, toluene, xylenes, chlorobenzene, dichlorobenzenes, trichlorobenzenes, chlorotoluenes, dichlorotoluenes, dichloroxylenes, bromobenzene, nitrobenzene, nitrotoluenes, and the like, hydrocarbons such as octanes, nonanes, decanes, decalin and the like, or mixtures thereof.

Though some of these solvents may undergo an oxidation during the reaction, this reaction velocity is much slower than that for the acenaphthenes, thus not substantially impeding the reaction of the acenaphthenes. On the contrary, it has been confirmed that, in some cases, the oxidation product or intermediate derived from such solvent serves to expedite the oxidation reaction of acenaphthenes. The lower fatty acid alone may be used as the solvent but mixtures of the lower fatty acid with other organic solvents indicated above are preferably used. The preferable solvent is a mixture of acetic acid and at least one solvent selected from the group consisting of benzene series, chlorobenzenes and nitrobenzenes. Most preferably, a mixture of acetic acid and chlorobenzene is employed. When mixed with other organic solvents, the lower fatty acid may preferably be used in an amount of at least 0.5 moles per mole of the starting acenaphthene to be oxidized. The solvent is preferably used in an amount of 2 to 20 times by weight as great as that of the acenaphthenes.

The reaction temperature is preferably in the range of above 30° C. to 150° C. Especially when the reaction temperature is increased as the reaction proceeds, e.g. using a temperature of 30° C. to 90° C. in an initial stage of the reaction and then a temperature of 90° C. to 140° C. in a last atage, good results can be obtained.

The partial pressure of oxygen in the reaction system is not critical but is generally in the range of 0.1 to 5 atmospheric pressures. A higher or lower pressure may be used. The whole amount of the starting material may be charged from the first or the material may be continuously charged together with the accelerator or reaction solvent.

The reaction is continued until absorption of oxygen is reduced to a very slight degree.

In case where the reaction does not proceed satisfactorily due to presence of an induction period, or when the reaction again sets in after it has been once stopped at a stage of reaction where the oxygen is absorbed to an insufficient extent, it will suffice, as well known in the art, to add a slight amount of an initiator such as of azobisisobutyronitrile or an organic peroxide such as hydroperoxide or the like.

Together with the heavy metal compound catalyst (1) and the accelerator (2), a promoter may be further added for facilitating the oxidation reaction. Aliphatic or aromatic tertiary amines, N,N-dialkyl-substituted amides and heterocyclic nitrogen-containing bases are usable for the above purpose. Examples of such promoter include triethylamine, N,N-dimethylbenzylamine, N,N-dimethylaniline, triethanolamine, dimethylformamide, dimethylacetamide, pyridine, quinoline, bipyridine, phenanthroline and the like. Though the action of the promoter is not clear it is believed that the promoter serves to suppress occurrence of violent reactions and side reactions by co-ordination with the metal compound, making the oxidation reaction proceed mildly. In fact, it has been experimentally found that the use of promoter permits the reaction to proceed stationarily without involving any sharp rise in absorption of oxygen at an initial stage of the reaction.

The promoter is generally used in an amount of 0.1 to 3 moles, preferably 0.2 to 2.5 moles, per mole of the heavy metal compound.

The obtained naphthalic acid is collected from the reaction solution by filtration or other suitable techniques. The reaction product obtained by oxidizing an acenaphthene in organic solvent with molecular oxygen in the presence of the catalyst, accelerator and, if desired, promoter may contain oxidation intermediates together with the intended naphthalic acid. In this case, the reaction system obtained by the first stage oxidation is subjected to distillation to remove the employed organic solvent therefrom and then treated in accordance with the procedure of the second stage oxidation described hereinbefore with or without separating the oxidation product from the distilled system. By the treatment, the intermediate contained in the oxidation product is further oxidized into a corresponding naphthalic acid. This treatment is considered very useful from viewpoints of yield and improvement in purity of the product. As described hereinbefore, the product obtained by oxidation with molecular oxygen in the first stage oxidation can be reoxidized by a process in which it is treated with a peroxide, a hypohalogenate, or molecular oxygen in an aqueous alkali solution or a mixed solvent of the alkali solution and organic solvent.

Though any preroxide or hypohalogenate may be usable in the reoxidation stage, aqueous hydrogen peroxide and sodium or pottassium hypochlorites are advantageous in an industrial sense. Oxygen gas or air is used as the molecular oxygen.

Any alkalis may be used and alkali hydroxides such as sodium hydroxide and potassium hydroxide are preferred for use as an aqueous solution of alkali. The organic solvents are those which are stable or inert in an oxidizing atmosphere in the presence of alkali. Examples of such solvent include aromatic hydrocarbons such as benzene, toluene, xylene, ethylbenzene, cumene and the like, nitro compounds such as nitrobenzene, nitrotoluenes, nitroxylenes and the like, halogenohydrocarbons such as chlorobenzene, dichlorobenzenes, trichlorobenzenes, chlorotoluenes, dichlorotoluenes, chloroxylenes, chloroethylbenzenes and the like, hydrocarbons such as octane, nonane, decane, cyclohexane, decalin, tetralin and the like, and ketones such as acetone, methyl ethyl ketone, methyl isopropyl ketone, diisopropyl ketone, cyclohexanone and the like. Under certain conditions, alcohols such as ethanol, propanols, butanols, cyclohexenol and the like may be used. These solvents may be used singly or in combination.

These organic solvents give a much pronounced effect of acceleration of the reaction when used in the reoxidation stage (second stage oxidation). In general, a mixed solvent of an aqueous alkali solution and an organic solvent is more advantageous than the alkali solution alone. The preferable mixed solvent is the mixture of the aqueous alkali solution and at least one benzene series, chlorobenzenes and nitrobenzenes, particularly, a mixed solvent of an aqueous alkali solution and chlorobenzene is preferred. If the organic solvent is insoluble in water, there may be used surface active agents or phase transfer catalysts such as tetrabutylammonium hydroxide, trimethylbenzylammonium hydroxide, triethylpyridinium bromide and the like.

The amount of the oxidizing agent varies depending on the oxidizing conditions of the first stage but is generally in the range of about 0.2 to 15 times by mole of acenapthenes.

The reaction temperature is generally in the range of 20° C. to about 110° C.

After completion of the reoxidation reaction, the organic solvent is recovered by separation or distillation. The remaining aqueous alkali solution is treated with active carbon, if necessary, and then admixed with an acid to allow an intended naphthalic acid to separate as crystals.

Naphthalic acids or acid anhydride which can be obtained in this invention include, for example, 4-chloro-naphthalic acid, 4,5-dichloro-naphthalic aid, 3,5-dichloro-naphthalic acid, 3,6-dichloro-naphthalic acid, 4-bromonaphthalic acid, 4,5-dibromonaphthalic acid, 3,5-dibromonaphthalic acid, 3-chloronaphthalic acid, 3-bromonaphthalic acid, 3-sulfonaphthalic acid, 4-sulfonaphthalic acid, 3-nitronaphthalic acid, 4-nitronaphthalic acid, 3,5-dinitronaphthalic acid, 4,5-dinitronaphthalic acid, 3,6-dinitronaphthalic acid, 3-sulfo-4-chloronaphthalic acid, 3-chloro-5-sulfonaphthalic acid, 4-chloro-5-sulfonaphthalic acid, 3-nitro-5-sulfonaphthalic acid, 3-nitro-4-chloronaphthalic acid, 3-chloro-4-nitronaphthalic acid, 3-chloro-5-nitronaphthalic acid or acid anhydride thereof, and the like.

The present invention will be particularly illustrated by way of the following examples.

EXAMPLE 1

There was provided a closed reaction system of a 100 ml flask equipped with a stirrer, a dropping funnel and a thermometer. This reaction system was so designed that when oxygen gas in the system was absorbed, oxygen gas was freshly supplemented so as to keep the inner pressure at atmospheric level. The flask were charged with 10 g of 5,6-dichloroacenaphthene, 0.4 g of cobalt acetate tetrahydrate, 0.02 g of manganese acetate tetrahydrate, 0.05 g of NaBr, 0.18 ml of triethanolamine, 20 ml of acetic acid, and 40 ml of chlorobenzene.

9 ml of acetic anhydride was introduced into the dropping funnel and the gas in the system was replaced by oxygen gas. When the reaction system was closed and heated up to 70° C., absorption of the oxygen gas was observed, demonstrating that the reaction set in. The acetic anhydride was gradually dropped to make the reaction proceed. About 3 hours after the dropping, it was found that 1000 ml of oxygen was absorbed. Then, the reaction system was heated to 80° C., to which was further dropwise added acetic anhydride for further reaction while heating the reaction system so that the reaction system reached 90° C. after 15 hours. After the reaction for further 8 hours, the amount of absorbed oxygen reached 2400 ml (96% of the theoretical) whereupon the amount of the dropped acetic anhydride was 9 ml. The reaction system was further gradually heated up to 110° C. at which the reaction was completed. The total reaction time was 40 hours. Part of the resulting crystals in the reaction mixture was sampled and subjected to an analysis, revealing that the crystals contained 79% of 4,5-dichloronaphthalic acid and 16% of 5,6-dichloroacenaphthenequinone.

Acetic acid was distilled off under reduced pressure from the reaction mixture and the resulting mixture was introduced into 150 ml of water dissolving 12 g of KOH, followed by agitating at 90° C. for 20 minutes. Thereafter, the chlorobenzene remaining in the mixture was recovered by steam distillation. The insoluble matter was removed by filtration from the aqueous solution to recover the metal catalyst in the form of a hydroxide. The filtrate was treated with hydrochloric acid to permit a precipitate to separate, followed by filtering, washing with water and drying at 120° C. for 5 hours to obtain 8.2 g of light brown 4,5-dichloronaphthalic anhydride in a yield of 69%.

EXAMPLE 2

10 g of 5,6-dichloroacenaphthene, 0.3 g of cobalt acetate tetrahydrate, 0.015 g of manganese acetate tetrahydrate, 0.03 g of NaBr, 0.18 ml of triethanolamine, 35 ml of chlorobenzene and 15 ml of acetic acid were charged into the same reactor as used in Example 1, and 8 ml of acetic anhydride was placed in the dropping funnel. When the gas in the system was replaced with oxygen gas and heated up to 68° C., the reaction set in and was continued while dropwise adding acetic anhydride thereto. 3 hours after commencement of the reaction, the amount of absorbed oxygen reached 1000 ml, and the system was then heated to 75° C., then to 85° C. after 2 hours, and finally to 90° C. after 3 hours. After the reaction for a total time of 18 hours, the consumption of oxygen reached 2300 ml. The acetic acid was distilled off from the resulting reaction mixture, and then the mixture was placed in a 300 ml flask. To the flask were added chlorobenzene until the total amount reached 100 ml and then 160 ml of water dissolving therein 12 g of KOH, followed by reacting for 1.5 hours at 60°-80° C. while dropping 20 ml of an aqueous 35% hydrogen peroxide solution. After the chlorobenzene was removed for recovery by steam distillation, 1 g of active carbon was added to the reaction mixture, and then removed by filtration. The resulting filtrate was admixed with an acid to permit precipitation, followed by filtering, washing with water and drying to obtain 10.9 g of light yellowish 4,5-dichloronaphthalic anhydride. The yield and purity were found to be 91% and 97.2%, respectively.

EXAMPLE 3

The reaction was conducted for 21 hours in the same procedure as in Example 2 using 0.08 g of phenanthroline instead of 0.18 ml of triethanolamine. The amount of absorbed oxygen was found to be 2340 ml. As a result, 10.5 g of light yellow 4,5-dichloronaphthalic anhydride was obtained in a yield of 88%.

EXAMPLE 4

Example 2 was repeated using two different heavy metal compounds indicated below instead of manganese acetate tetrahydrate, the results being shown below.

| Heavy Metal Catalyst | First Stage Oxidation Reaction Time | Amount of Absorbed Oxygen | Yield |
| --- | --- | --- | --- |
| (1) cerium acetate monohydrate 0.021g | 20 hours | 2220 ml | 10.2g (85%) |
| (2) chromium | 18 hours | 1970 ml | 9.7g (81%) |
| acetate monohydrate 0.1g | | | |

EXAMPLE 5

Example 2 was repeated for conducting the first stage oxidation. The resulting reaction mixture obtained by oxidation with oxygen gas was subjected to a filtration to obtain a reaction product. The thus obtained product was mixed with 70 ml of chlorobenzene, 12 g of KOH and 130 ml of water and agitated, to which was further dropwise added, at 40° C., 28 ml of an aqueous sodium hypochlorite solution having an effective chlorine concentration of 7%. The temperature was raised up to 90° C. and the reaction was continued for 5 hours. The chlorobenzene was removed from the reaction solution by distillation, to which was added 1 g of active carbon. After agitation, the active carbon was removed by filtration and the filtrate was mixed with hydrochloric acid for permitting precipitation, followed by filtering, washing with water and drying to obtain 8.5 g (yield of 71%) of light yellow 4,5-dichloronaphthalic anhydride.

The reason why the yield is lower than that of Example 2 is due to a fact that the crude product obtained by the first stage oxidation was separated by filtration (the filtrate contains, in dissolved form, the intended product) and an intermediate which was to be converted into the final product if treated by the second stage oxidation. These dissolved substances may be collected and recycled to the oxidation stage.

Similar results were obtained when the above procedure was repeated using an aqueous potassium hypochlorite solution having the same effective chlorine concentration as used above instead of the aqueous sodium hypochlorite solution.

EXAMPLE 6

The reaction product obtained in the same manner as in Example 5 was filtered and mixed with 25 ml of chlorobenzene, 12 g of KOH and 200 ml of water, followed by agitating and heating from 40° C. to 80° C. in 2.5 hours while injecting oxygen gas at a rate of 10 ml/min. After completion of the second stage oxidation reaction, the resulting reaction solution was treated in the same manner as in Example 5 to obtain 8.6 g of 4,5-dichloronaphthalic anhydride in a yield of 72%. The anhydride was obtained in the form of slightly brownish crystals and was usable as a starting material for dyes and pigments.

EXAMPLE 7

8 g of sodium acenaphthene-5-sulfonate, 0.4 g of cobalt acetate tetrahydrate, 0.02 g of manganese acetate tetrahydrate, 0.05 g of NaBr and 40 ml of acetic acid were charged together and heated up to 70° C. while blowing air into the reaction system at a rate of 50 ml/min. Because of presence of an induction period, 0.1 ml of methyl ethyl ketone peroxide (55% solution in dimethylphthalate) was added to the system. The reaction was conducted while dropping acetic anhydride. 5 hours after commencement of the reaction, the system was heated to 80° C. and then to 90° C. after further 4 hours and was maintained at 90° C. for 14 hours. The reaction was carried out for a total time of 23 hours, during which 9 ml of acetic anhydride was added. The reaction mixture was concentrated to about 15 ml, cooled, filtered, washed first with small amount of acetic acid and then water, and dried to obtain 5.5 g of sodium naphthalic acid anhydride sulfonate. The yield was found to be 59%.

EXAMPLE 8

The oxidation reaction was conducted in the same manner as in Example 2 using 10 g of 5-nitroacenaphthene instead of 5,6-dichloroacenaphthene and also using methyl ethyl ketone peroxide as a reaction initiator because an induction period was long. The reaction was carried out for 25 hours in total while heating the system from 68° C. to 90° C., during which 2460 ml of oxygen was absorbed. Acetic anhydride used was 12 ml. The reaction solution was cooled, filtered, washed with 10 ml of acetic acid and then water, and dried to obtain 8.2 g of yellowish white 5-nitronaphthalic anhydride in a yield of 67.2%.

EXAMPLE 9

10 g of 5,6-dichloroacenaphthene, 0.3 g of cobalt acetate tetrahydrate, 0.003 g of manganese acetate tetrahydrate, 0.2 g of NaBr, 50 ml of chlorobenzene and 8 ml of acetic acid were charged into a reaction vessel of the same type as used in the foregoing examples and heated up to 70° C., into which oxygen gas was blown for reaction while dropping methyl ethyl ketone used as an accelerator. The reaction system was gradually heated from 70° C. to 90° C. in 20 hours, during which 15 ml of methyl ethyl ketone was added. After completion of the reaction, the system was cooled and the resulting crystals were separated by filtration and washed with ethanol. The cake was placed in a mixed solvent composed of 200 ml of water dissolving therein 10 g of KOH and 50 ml of toluene and subjected to the second stage oxidation at 60°–80° C. while dropping 20 ml of an aqueous 30% hydrogenperoxide solution. After completion of the oxidation reaction, the toluene was removed by steam distillation and the remaining solution was treated with active carbon, which was then removed by filtration. The filtrate was treated with an acid to allow precipitation, followed by filtering, washing with water and drying to obtain 9.1 g of 4,5-dichloronaphthalic anhydride in a yield of 76%.

Similar results were obtained when the second stage oxidation was conducted in the same manner as indicated above using toluene instead of nitrobenzene.

EXAMPLE 10

Example 9 was repeated using 0.25 g of CaBr instead of NaBr thereby obtaining 9.0 g of 4,5-dichloronaphthalic anhydride. The yield was found to be 75%.

EXAMPLE 11

0.9 g of cobalt acetate tetrahydrate, 0.09 g of manganese acetate tetrahydrate, 0.08 g of NaBr, 0.3 ml of triethanolamine, 60 ml of acetic acid and 30 ml of o-dichlorobenzene were charged into a 300 ml glass autoclave and heated to 68° C. The inner pressure was kept at 3.5 kg/cm$^2$. A suspension of 20 g of 5,6-dichloroacenaphthene in 40 ml of o-dichlorobenzene was prepared and divided into five batches, which were stepwise added under pressure to the reaction system while passing air from a bomb to the reaction system and also acetic anhydride from a pump under pressure. The whole amount of 5,6-dichloroacenaphthene was charged in 3 hours. Thereafter, the reaction system was gradually heated up to 90° C. in 8 hours. At the temperature of 90° C. the air flow rate was reduced to half and the reaction was continued for further 5 hours. After stopping the dropping of acetic anhydride and the passage of air, the reaction mixture was allowed to stand for 4 hours. The total amount of acetic anhydride added was found to be 17 ml.

The reaction mixture was cooled to allow crystals to precipitate and the crystals were separated by filtration.

The thus separated crystals were heated under agitation together with 60 ml of o-dichlorobenzene, 25 g of potassium hydroxide and 300 ml of water, into which was dropped 32 ml of aqueous hydrogen peroxide (35%) at 60°–80° C. After reaction for 4 hours at the temperature, the o-dichlorobenzene was removed by steam distillation and 3 g of active carbon was added to the remaining solution, followed by cooling and filtering. The filtrate was treated with hydrochloric acid to permit precipitation. The resulting crystals were separated by filtration, washed with water to obtain 17.3 g of 4,5-dichloronaphthalene-1,8-dicarboxylic anhydride in a yield of 72%.

EXAMPLE 12

There was provided a 300 ml flask which was equipped with an agitator and a thermometer and provided with a gas feed port and a gas exhaust port attached with a condenser. The flask was charged with 22.3 g of 5,6-dichloroacenaphthene, 0.6 g of cobalt acetate tetrahydrate, 0.2 g of manganese acetate tetrahydrate, 0.2 g of NaBr, 10 ml of acetic acid, 90 ml of chlorobenzene, and 17 ml of acetic anhydride. The reaction system was heated to 65° C., into which air was blown for oxidation at a rate of 50 ml/min. The reaction was continued for 20 hours, during which the system was gradually heated up to 95° C. After completion of the reaction, the acetic acid was removed by distillation together with the chlorobenzene. To the remaining reaction mixture were added 50 ml of chlorobenzene and 400 ml of water dissolving therein 27 g of KOH, into which 32 ml of a sodium hypochlorite solution (13.6%) was dropped at 70°–100° C. The chlorobenzene was removed from the reaction solution, followed by treating with active carbon and filtering. The filtrate was treated with an acid to permit precipitation and the precipitate was filtered, washed with water and dried to obtain 23.5 g of 4,5-dichloronaphthalic anhydride. The yield was 88.0%.

EXAMPLE 13

Example 12 was repeated for oxidizing 18.9 g of 5-chloroacenaphthene except that the amounts of manganese acetate tetrahydrate and chlorobenzene were 0.1 g and 50 ml, respectively. As a result, 19.8 g of light yellow 4-chloronaphthalic anhydride was obtained. The yield was found to be 85.0%.

EXAMPLE 14

18.9 g of 5-chloroacenaphthene, 0.4 g of cobalt acetate tetrahydrate, 0.65 g of manganese acetate tetrahydrate, 0.2 g of NaBr, 20 ml of acetic acid, and 40 ml of benzene were charged into a reaction vessel, into which air was blown at a rate of 60 ml/min from a temperature of 65° C. The content was gradually heated up to 80° C. in 26 hours. 14 ml, in total, of acetic anhydride was dropwise added to the reaction system over the reaction time. After completion of the reaction, the solvents were removed by distillation. To residue were added 100 ml of tert-butanol and 500 ml of water dissolving 20 g of NaOH therein, to which was dropwise added 9 g of an aqueous 30% hydrogen peroxide solution at 60°–80° C. 2 hours after the dropping, the tert-butanol was removed by steam distillation. The remaining solution was treated in the same manner as in Example 8 to obtain 19.2 g of 4-chloronaphthalic anhydride in a yield of 83%.

EXAMPLE 15

23.3 g of 5-bromoacenaphthene was oxidized in the same manner as in Example 12 thereby obtaining 23.0 g of light yellowish brown 4-bromonaphthalic anhydride in a yield of 83%.

EXAMPLE 16

8 g of acenaphthene, 0.45 g of cobalt acetate tetrahydrate, 0.045 g of manganese acetate tetrahydrate, 0.045 g of NaBr, 0.17 ml of triethanolamine, 30 ml of acetic acid, and 50 ml of chlorobenzene were charged in the same manner as in Example 1. The air in the system was substituted with oxygen gas and the system was heated to 65° C., the reaction setting in. Acetic anhydride was dropped while gradually heating the reaction system for reaction. The reaction was continued for 42 hours during which the reaction temperature was increased up to 90° C. The total amount of absorbed oxygen reached 3170 ml and acetic anhydride was added in an amount of 7 ml. After completion of the reaction, the reaction mixture was cooled to allow crystals to precipitate and the crystals were separated by filtration, washed with water and dried to obtain 8.1 g of yellowish white naphthalic anhydride (yield 79%).

The similar result was obtained when the above procedure was repeated using 4 g of paraformaldehyde instead of acetic anhydride. In this case paraformaldehyde was charged at the beginning of the reaction. Yield 77%.

EXAMPLE 17

10 g of 5,6-dichloroacenaphthene, 0.45 g of cobalt acetate tetrahydrate, 0.045 g of manganese acetate tetrahydrate, 50 ml of chlorobenzene and 30 ml of acetic acid were charged in the same manner as in Example 1. The air in the system was substituted with oxygen gas and acetic anhydride was dropped into the system for reaction at 75° C. 4.5 hours after the dropping, the system was heated to 88° C. and, after 7 hours, 0.1 g of cobalt acetate tetrahydrate and 0.03 g of manganese acetate tetrahydrate were further added to the system. The reaction was further continued and it was observed that no oxygen was absorbed for 40 hours, in total, after commencement of the reaction. The amount of absorbed oxygen reached 1910 ml (76% of the theoretical).

The reaction mixture was subjected to a reduced pressure distillation to remove the acetic acid therefrom and introduced into a 300 ml flask, to which small amount of chlorobenzene was added to make the total amount 60 ml. To the system was further added a solution of 12 g of potassium hydroxide in 150 g of water, followed by dropping 18 ml of 35% hydrogen peroxide in 5 hours for reaction at 50°–60° C. After completion of the reaction, the chlorobenzene was removed by steam distillation. The remaining aqueous solution was introduced with 1 g of active carbon, cooled to room temperature, and filtered to collect the catalyst. The filtrate was treated with an acid to allow precipitation, filtered, washed with water and dried to obtain 7.8 g of yellowish white 4,5-dichloronaphthalic acid anhydride. The yield was 65%.

EXAMPLE 18

The reaction was effected in the same manner as in Example 17 using 0.02 g of dibromoacrylic acid instead 0.1 g of Co acetate tetrahydrate and 0.3 g by Mn acetate tetrahydrate. 28 hours after commencement of the reaction, the absorption of oxygen became very slow, at which the amount of absorbed oxygen reached 2335 ml. The reaction mixture was cooled and the resulting crystals were separated by filtration. The crystals were washed with small amount of ethanol and were mixed with 20 g of KOH and 300 ml of water and agitated, into which 30 ml of an aqueous 35% hydrogen peroxide solution for reaction at 80°–95° C. for 5 hours. After completion of the reaction, the entirety was cooled and subjected to filtration at room temperature. 0.9 g of the insoluble matter was found to be contained. The filtrate was subjected to an acid treatment for permitting precipitation, filtered, washed with water and dried to obtain 8.2 g of 4,5-dichloronaphthalic acid anhydride. The yield was 68%.

What is claimed is:

1. A process for producing naphthalic acid or anhydride thereof, which comprises oxidizing an acenaphthene selected from the group consisting of 5,6-dichloroacenaphthene, 5-chloroacenaphthene, 5-bromoacenaphthene and sodiumacenaphthene-5-sulfonate with molecular oxygen in an organic solvent at a temperature of 30° to 150° C. in the presence of (1) a catalyst which is either (a) a mixture of cobalt salts and other heavy metal salts in which the atomic ratio of cobalt to one of said metals other than cobalt is in the range of 1:0.001 to 2, said mixture being in an amount of 0.005 to 0.3 mole per mole of said acenaphthene derivatives, or (b) a mixture of said (a), and a bromine compound in the range of $5 \times 10^{-5}$ to $2 \times 10^{-1}$ mole/liter of the reaction solution; and (2) at least one accelerator selected from the group consisting of a lower fatty acid anhydride, ketone and an aldehyde, and further oxidizing the thus obtained oxidation product with an oxidant selected from the group consisting of a peroxide, hypohalogenate and molecular oxygen in an aqueous alkali solution or a mixture of an aqueous alkali solution and an organic solvent.

2. A process according to claim 1, wherein said accelerator is a lower fatty acid anhydride.

3. A process according to claim 2, wherein said lower fatty acid anhydride is acetic anhydride.

4. A process according to claim 1, wherein said heavy metal compound catalyst is a mixture of cobalt and manganese salts.

5. A process according to claim 1, wherein said catalyst is a mixture of a cobalt salt, a manganese salt and an alkali metal bromide or alkaline earth metal bromide.

6. A process according to claim 1, wherein said heavy metal compound catalyst is a salt of a fatty acid containing 2 to 10 carbon atoms.

7. A process according to claim 1, wherein said organic solvent is a mixture of acetic acid and at least one solvent selected from the group consisting of the benzene series, chlorobenzenes or nitrobenzenes.

8. A process according to claim 7, wherein said mixture is a mixture of acetic acid and chlorobenzene.

9. A process according to claim 1, wherein the mixture in the second stage oxidation is that of the aqueous alkali solution and at least one benzene series, chlorobenzenes or nitrobenzenes.

10. A process according to claim 1, wherein the mixture is that of the aqueous alkali solution and chlorobenzene.

11. A process according to claim 1, wherein the oxidizing agent in the second stage is aqueous hydrogen peroxide, sodium hypochlorite or potassium hypochlorite.

12. A process according to claim 1, wherein the reaction temperature in the second oxidation stage is in the range of 20° to 110° C.

* * * * *